United States Patent [19]

Pasternack

[11] Patent Number: 5,072,728

[45] Date of Patent: Dec. 17, 1991

[54] RECIRCULATING RESPIRATOR

[75] Inventor: Adalbert Pasternack, Bad Schwartau, Fed. Rep. of Germany

[73] Assignee: Drägerwerk AG, Lübeck, Fed. Rep. of Germany

[21] Appl. No.: 580,270

[22] Filed: Sep. 7, 1990

[30] Foreign Application Priority Data

Sep. 12, 1989 [DE] Fed. Rep. of Germany ....... 3930362

[51] Int. Cl.$^5$ ........................ A61M 16/00; A62B 7/00

[52] U.S. Cl. .......................... 128/204.18; 128/205.22; 128/205.13; 128/205.12; 128/205.24

[58] Field of Search ...................... 128/204.18, 205.12, 128/204.21, 205.22, 205.24, 205.23, 205.13

[56] References Cited

U.S. PATENT DOCUMENTS

| | | | |
|---|---|---|---|
| 2,406,888 | 8/1946 | Meidenbauer | 128/205.25 |
| 2,456,130 | 12/1948 | Lambertsen | 128/205.22 |
| 3,805,779 | 4/1974 | Kowalski | 128/202.22 |
| 3,923,056 | 12/1975 | Bingmann et al. | 128/204.21 |
| 3,957,044 | 5/1976 | Fletcher et al. | 128/202.22 |
| 4,302,640 | 11/1981 | Vicenzi et al. | 128/202.22 |
| 4,440,166 | 4/1984 | Winkler et al. | 128/204.22 |
| 4,498,470 | 2/1985 | Warncke | 128/205.12 |
| 4,567,889 | 2/1986 | Lehmann | 128/204.28 |
| 4,667,669 | 5/1987 | Pasternack | 128/204.28 |

*Primary Examiner*—Edgar S. Burr
*Assistant Examiner*—Lisa Malvaso
*Attorney, Agent, or Firm*—McGlew & Tuttle

[57] ABSTRACT

The present invention pertains to a recirculating respirator for positive pressure operation, in which it is possible to switch off the elements generating the over pressure in case of excessively high oxygen consumption.

A flow-measuring device is provided in the oxygen supply line, which is connected to a control unit. A warning device 36, and a switching device, for switching off the over pressure is also provided.

11 Claims, 1 Drawing Sheet

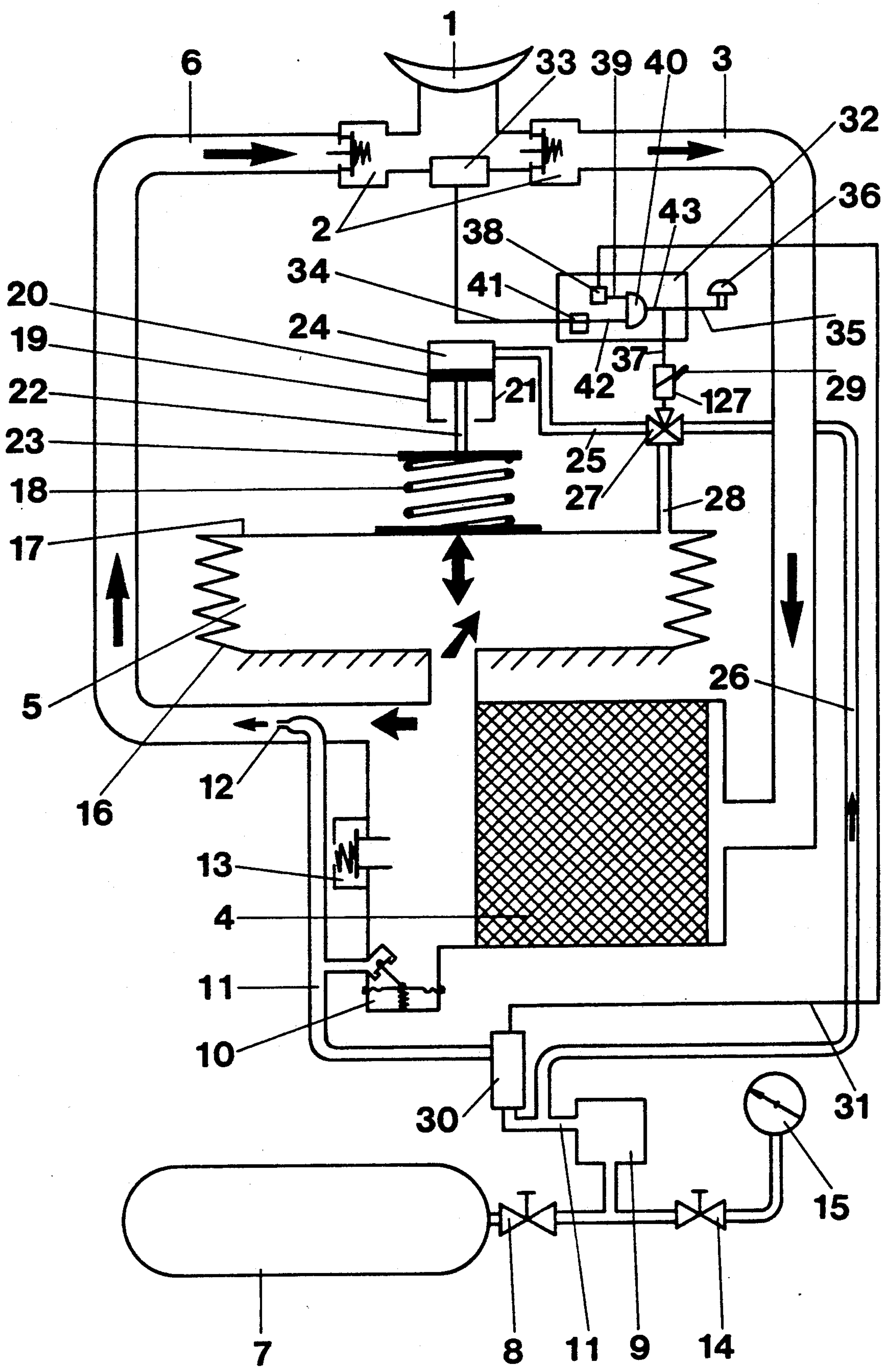
1
6
33
39
40
3
32
2
36
43
38
34
41
20
24
35
19
37
21
42
127
29
22
25
23
27
28
18
17
26
5
16
12
13
4
11
10
30
31
15
7
8
11
9
14

RECIRCULATING RESPIRATOR

FIELD OF THE INVENTION

The present invention pertains to a recirculating respirator for positive pressure operation including an arrangement for switching off of the elements generating the over pressure in the case of excessively high oxygen consumption.

BACKGROUND OF THE INVENTION

If a leak develops in the system of a recirculating respirator with positive pressure operation, e.g., due to the oxygen mask being put on incorrectly, the time during which the respirator can be used is greatly reduced by the great loss of oxygen caused by the over pressure conditions. This may lead to a dangerous situation for the user of the respirator. If the device switches over from positive pressure operation to normal operation in case of a leak, the loss of oxygen will be reduced.

Such a respirator has been known from West German Patent No. DE-PS 32,29,240. This device has a blocking mechanism which eliminates the positive pressure operation and is actuated automatically in case of a leak. This blocking mechanism is designed as a cylinder-piston unit, wherein the movement of the piston is coupled with the movement of the breathing bag. At the same time, the force applied by the piston to the breathing bag via a lever generates the over pressure in the system. The cylinder-piston unit has an outlet valve which opens when a defined stroke position of the piston is exceeded, so that the over pressure in a chamber above the piston is eliminated and the further supply of pressurized oxygen is blocked by an intake valve responding to the pressure reduction in the chamber. As a result, the piston no longer applies a force to the breathing bag, and the device operates in the normal standard-pressure mode. When another defined stroke position of the piston is exceeded, the outlet valve is closed and the intake valve is opened, so that the force for inducing the positive pressure operation is again available. The complicated mechanical design with many sealing members, the lack of an unambiguous recognition of a leak from a single, defined position of the breathing bag, and the lack of information on the existence of a leak for the user of the device are disadvantages of this device.

SUMMARY AND OBJECTS OF THE INVENTION

It is an object of the present invention to provide a recirculating respirator with automatic over pressure shut-off in the case of a leak, which can be realized without complicated mechanical constructions, which permits the most unambiguous leak detection possible, and which informs the user of the device of the presence of a leak.

To accomplish this task the device has a flow rate measuring means in the oxygen supply line, which is connected to other components.

The advantages of the present invention are that complicated mechanical designs can be dispensed with, leaks can be detected with certainty by monitoring the rate of oxygen consumption, and it is possible to warn the user of the device of a leak in the breathing circuit. The flow rate measuring means detects the rate of oxygen consumption directly at the source, without interference with structures and components in the rest of the breathing circuit.

The flow rate measuring means may be designed as a flow sensor of known design, for example, a vane type flow sensor. In this case, it is preferably arranged in the low-pressure part of the oxygen supply line. It is also possible to use as a flow rate measuring means a pressure sensor which measures the gas pressure in the oxygen tank, with a downstream time integration unit, because if the volume of the oxygen tank is known, the rate of oxygen discharged can be inferred from the pressure reduction. A residual pressure warning can additionally be realized with the pressure sensor.

The flow rate measuring means is connected to a control unit in which the measured flow rate is compared to a preselectable limit value. If the measured value exceeds the limit value, the control unit sends a signal. This signal can be used to activate a warning device, e.g., a sound generator. The user of the device is thus informed of increased oxygen consumption. If the increased oxygen consumption is not caused by heavy physical activity of the user of the device, he must assume that there is a leak in the breathing circuit. If this leak cannot be eliminated, e.g., by correcting the position of a slipped mask, the user of the device can reduce the loss of oxygen from the respirator by switching off the positive pressure operation manually.

In another variant of the present invention, the signal generated by the control unit when the predetermined limit value of the oxygen supply is exceeded activates a device which switches off the positive pressure operation without involvement of the user of the device. At the same time, the warning device is activated in order to inform the user of the device of the changed mode of operation of the respirator and the increased oxygen consumption.

The control unit may also be designed to detect two limit values of the oxygen consumption. When the first limit value is exceeded, the warning device is activated by a signal. The user of the device ca then decide for himself whether or not to switch off the positive pressure operation. When a second, higher limit value is exceeded, the positive pressure operation is switched off automatically.

In order to clearly distinguish a leak in the system from high oxygen consumption by the user of the device, monitoring of the oxygen consumption by the flow rate measuring means can be synchronized with the phase of expiration of the user of the device. Oxygen consumption detected during this phase can only be due to a leak in the system.

A pressure sensor in the breathing circuit, preferably in the respiration gas connection of the user of the device, may serve as a sensor for detecting the expiration phase. The pressure in the breathing circuit decreases during the inspiration phase and increases again during the expiration phase. The expiration phase can be identified from these pressure fluctuations, which can be recognized with the pressure sensor. The signal of the control unit, which indicates an oxygen consumption exceeding a predetermined limit value, is associated with a signal marking the expiration phase in a logic circuit, so that an output signal is generated only when the limit value of the oxygen consumption is exceeded during the expiration phase. This limit value may be selected to be substantially lower than in the above-described embodiments of the present invention, which do not comprise recognition of the expiration phase. It is thus possible to recognize even a small leak in the system.

A device for switching off the positive pressure operation and a warning device can be activated by the above-mentioned output signal of the logic circuit.

It is a further object of the invention to provide a recirculating respirator providing both over pressure and normal operation conditions which is simple in design, rugged in construction and economical to manufacture.

While a specific embodiment of the invention has been shown and described in detail to illustrate the application of the principles of the invention, it will be understood that the invention may be embodied otherwise without departing from such principles.

The only figure is a schematic view showing the recirculating respirator arrangement according to the invention.

DETAILED DESCRIPTION OF THE PREFERRED EMBODIMENT

Referring to the drawing in particular, the recirculating respirator for positive pressure operation, is represented schematically in the only figure. The components forming the breathing circuit are shown in the functional arrangement on a support frame with an outer protective jacket. These include a respiration connection 1 with check valves 2, an expiration line 3, a regenerating cartridge 4 binding the carbon dioxide present in the exhaled air, a breathing bag 5, and an inhalation line 6. The oxygen consumed during respiration is replaced from an oxygen tank 7 serving as the pressurized gas source into the breathing circuit behind the breathing bag 5, via a cylinder valve 8, a pressure-reducing valve 9, a demand oxygen system 10, as well as via a pipeline 11 with a constant metering unit 12. A pressure relief valve 13 positioned behind the regenerating cartridge 4 prevents an unacceptably high pressure from occurring in the breathing circuit. A pressure gage 15 is connected to the oxygen tank 7 via a valve 14 for checking the oxygen reserve.

The breathing bag 5 consists of bellows 16 closed by a movable, rigid front wall 17.

The over pressure means generating the positive pressure or over pressure condition in the breathing circuit are designed as a combination of a spring 18 and a single-acting cylinder-piston unit 19 comprising a piston 20 which is arranged displaceably in a cylinder 21. The cylinder 21 is open on the side facing the spring 18, and the displaceable piston 20 is connected to the end of the spring 18 facing away from the breathing bag 5 via a piston rod 22 and the spring plate 23. The other end of the spring 18 rests on the front wall 17 of the breathing bag 5.

A partial space 24 of the cylinder, which space is connected to the pipeline 11 via a line section 25 and a pressurized gas line 26, is located above the piston 20.

The pressurized gas line 26 contains as a change-over valve, a solenoid valve 27 with an actuating magnet 127. By this arrangement the pressurized gas line 26 can be closed and separated from the cylinder partial space 24, wherein the solenoid valve 27, and actuating magnet 127 establishes the communication between the cylinder partial space 24 and the breathing bag 5 via a vent line 28. The change-over valve can be changed over manually by means of a hand lever 29.

A flow-measuring device or flow rate measuring means 30 is arranged in the pipeline 11. It is connected to a control unit 32 via a signal line 31. A pressure sensor 33, which is connected to the control unit 32 via a signal line 34, is arranged in the respiration connection 1. A sound generator 36, serving as a warning device, is connected to the control unit 32 via a signal line 35, and the solenoid valve 27, and actuating magnet 127 as connected to the control unit via signal line 37.

In the normally occurring positive pressure operation of the respirator, the solenoid valve 27, and actuating magnet 127 as connected so that oxygen enters the cylinder-piston unit 19 under pressure from the pressure-reducing valve 9 via the pressurized gas line 26 and the line section 25. As a result, the piston 20 moves into the lower end position, thus tensioning the spring 18. The spring 18 therefore applies a force to the front wall 17 of the breathing bag 5, as a result of which positive pressure builds up in the breathing circuit.

The amount of oxygen fed through the pipeline 11 into the breathing circuit is measured by the flow-measuring device 30 designed as a flow sensor. The measured value is sent to the control unit 32 via the signal line 31, and is evaluated by a limit value circuit 38. If the measured value exceeds a preselectable limit value, the limit value circuit 38 sends a signal to an input 39 of a logic circuit 40.

A pressure sensor 33 , which measures the pressure in the respiration connection 1 is arranged in the respiration connection 1 and can be used as a respiration phase sensor. The measured value is sent to the control unit 32 via a signal line 34 . The pressure rise characteristic of the expiration phase of the user of the device is recognized by means of a limit value circuit 41 . The limit value circuit 41 sends a signal to the second input 42 of the logic circuit 40 during the expiration phase.

The logic circuit links the two signals on its inputs 39, 42, so that its output 43 will carry a signal when the predetermined limit value of the amount of oxygen is exceeded during the expiration phase. This signal unambiguously marks a leak in the breathing circuit. The output signal of the logic circuit 40 activates the sound generator 36 serving as a warning device, which is connected via the signal line 35 . The user of the device is warned of the presence of a leak in the breathing circuit by the acoustic signal of the sound source 36, so that the user is able to try to take appropriate countermeasures. At the same time, the solenoid valve 27, and actuating magnet 127 are switched over by the output signal of the logic circuit 40. As a result, the cylinder partial space 24 is vented, the spring 18 is released, and the over pressure in the breathing circuit is eliminated, which considerably reduces the oxygen loss caused by the leak. Using the hand lever 29, the positive pressure operation can also be switched off manually.

While a specific embodiment of the invention has been shown and described in detail to illustrate the application of the principles of the invention, it will be understood that the invention may be embodied otherwise without departing from such principles.

What is claimed is:

1. A recirculating respirator for positive pressure operation, comprising:

a breathing circuit for supplying respiratory gas to a patient including an inhalation connection and an exhalation connection; over pressure means connected to said breathing circuit for generating an over pressure condition in said breathing circuit, said over pressure means being switchable between an over pressure condition and a normal condition;

respiratory gas supply circuit connected to said breathing circuit including a respiratory gas supply line; flow rate measuring means, positioned in said respiratory gas supply line, for generating a signal representing rate flow in said respirator gas supply line; and, control unit means for receiving said respirator supply line flow rate signal, and connected to said over pressure means for switching said over pressure means between said over pressure condition and said normal condition, dependent on said flow rate.

2. A recirculating respirator according to claim 1, further comprising a respiration phase sensor connected to said breathing circuit; said control unit means including a logic circuit receiving said flow rate signal from said flow rate measuring means and for receiving a signal from said respiration phase sensor and for generating a control signal when a preselected means respiratory gas consumption is exceeded during an expiration phase.

3. A recirculating respirator according to claim 1, wherein said flow rate measuring means includes a flow sensor.

4. A recirculating respirator according to claim 1, wherein said flow rate measuring means includes a pressure sensor connected to a high pressure supply tank and a unit for integrating the measured pressure values over time.

5. A recirculating respirator according to claim 1, wherein: said control unit means connected to said flow rate measuring means for generating a signal when a preselected, mean rate of gas consumption is exceeded.

6. A recirculating respirator according to claim 5, wherein said control unit means includes logic circuit means for receiving a signal that a preselected, mean rate of gas consumption has been exceeded and receiving a respiration phase signal from a respiration phase sensor and for generating a signal when a preselected, means rate of gas consumption is exceeded during the expiration phase.

7. A recirculating respirator according to claim 6, wherein said respiration phase sensor is a pressure sensor positioned in the breathing circuit means.

8. A recirculating respirator according to claim 5, wherein a warning device is connected to said control unit means, said warning device being activatable by said control unit means.

9. A recirculating respirator according to claim 8, further comprising manual activation means for switching said breathing circuit from an over pressure condition to a normal condition.

10. A recirculating respirator according to claim 5, further comprising: over pressure means for generating said over pressure condition and actuator means connected to said control unit means for reactivating said over pressure means.

11. A recirculating respirator according to claim 10, wherein said control unit means is connected to a warning device for activating said warning device when a first, preselected mean rate of gas consumption is exceeded and for activating said actuator means for deactivating said over pressure means when a second preselected, higher rate of gas consumption is exceeding.

* * * * *